(12) United States Patent
Nakashima et al.

(10) Patent No.: US 6,990,175 B2
(45) Date of Patent: Jan. 24, 2006

(54) X-RAY COMPUTED TOMOGRAPHY APPARATUS

(75) Inventors: Shigeyuki Nakashima, Yaita (JP); Yuji Yanagida, Otawara (JP); Toshiyuki Shinno, Otawara (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 10/262,896

(22) Filed: Oct. 3, 2002

(65) Prior Publication Data

US 2003/0076927 A1 Apr. 24, 2003

(30) Foreign Application Priority Data

Oct. 18, 2001 (JP) ............................ 2001-320927

(51) Int. Cl.
*A61N 5/10* (2006.01)
*H05G 1/70* (2006.01)
(52) U.S. Cl. ............................ 378/65; 378/9; 378/14; 378/17; 378/92; 378/101; 378/150
(58) Field of Classification Search ............... 378/4, 378/5, 9, 11, 14, 17, 65, 92, 101, 147, 150, 378/151, 152, 197
See application file for complete search history.

(56) References Cited

U.S. PATENT DOCUMENTS

| | | | | | |
|---|---|---|---|---|---|
| 4,345,158 | A | * | 8/1982 | Pfeiler et al. ................... | 378/5 |
| 4,998,268 | A | * | 3/1991 | Winter ........................ | 378/663 |
| 5,377,252 | A | * | 12/1994 | Liebetruth ................... | 378/151 |
| 5,490,196 | A | * | 2/1996 | Rudich et al. .............. | 378/101 |
| 5,661,773 | A | * | 8/1997 | Swerdloff et al. ............ | 378/65 |
| 5,751,781 | A | * | 5/1998 | Brown et al. ................. | 378/65 |
| 5,799,054 | A | * | 8/1998 | Hum et al. .................... | 378/17 |
| 5,818,902 | A | * | 10/1998 | Yu .............................. | 378/65 |
| 5,949,843 | A | * | 9/1999 | Tamaki et al. ................ | 378/17 |
| 5,966,422 | A | * | 10/1999 | Dafni et al. ................... | 378/9 |
| 6,198,790 | B1 | * | 3/2001 | Pflaum ......................... | 378/9 |
| 6,385,288 | B1 | | 5/2002 | Kanematsu ................... | 378/65 |
| 6,421,412 | B1 | * | 7/2002 | Hsieh et al. .................. | 378/9 |
| 6,661,870 | B2 | * | 12/2003 | Kapatoes et al. ............. | 378/65 |
| 2004/0005027 | A1 | * | 1/2004 | Nafstadius ................... | 378/65 |

\* cited by examiner

*Primary Examiner*—Allen C. Ho
(74) *Attorney, Agent, or Firm*—Oblon, Spivak, McClelland, Maier & Neustadt, P.C.

(57) ABSTRACT

An X-ray computed tomography apparatus includes a first X-ray tube configured to generate X-rays with which a subject to be examined is irradiated, a first X-ray detector configured to detect X-rays transmitted through the subject, a second X-ray tube which generates X-rays with which a treatment target of the subject is irradiated, a rotating mechanism which rotates the first X-ray tube, the first X-ray detector, and the second X-ray tube around the subject, a reconstructing unit configured to reconstruct an image on the basis of data detected by the first X-ray detector, and a support mechanism which supports the second X-ray tube. The central axis of X-rays from the second X-ray tube tilts with respect to a body axis of the subject. This makes it possible to reduce the dose on a portion other than a treatment target.

17 Claims, 7 Drawing Sheets

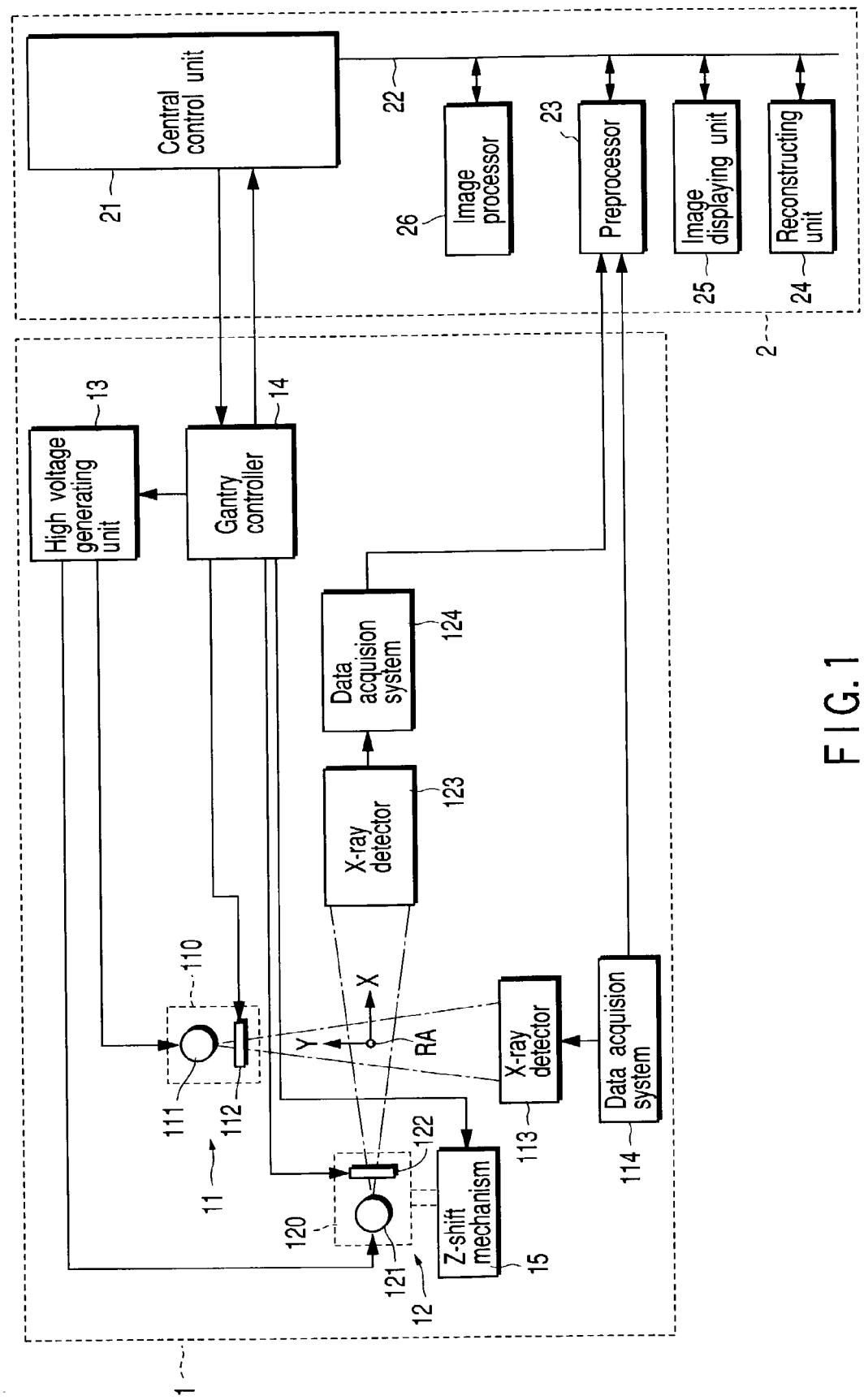
F I G. 1 ized image to obtain medical information such as the position, size, and degree of morbidity of a treatment target, and plans a radiotherapy treatment operation based on the information. That is, the doctor sets an irradiation range, irradiation position, dose, and the like. One of the biggest purposes of the treatment plan is to exclusively irradiate the treatment target (tumor) with radiation.

X-RAY COMPUTED TOMOGRAPHY APPARATUS

CROSS-REFERENCE TO RELATED APPLICATIONS

This application is based upon and claims the benefit of priority from the prior Japanese Patent Application No. 2001-320927, filed Oct. 18, 2001, the entire contents of which are incorporated herein by reference.

BACKGROUND OF THE INVENTION

1. Field of the Invention

The present invention relates to a multi-tube type X-ray computed tomography apparatus.

2. Description of the Related Art

Conventionally, X-ray computed tomography apparatuses which generate image data from the data (projection data) of X-rays transmitted through a subject to be examined have been known. A doctor refers to the generated image to obtain medical information such as the position, size, and degree of morbidity of a treatment target, and plans a radiotherapy treatment operation based on the information. That is, the doctor sets an irradiation range, irradiation position, dose, and the like. One of the biggest purposes of the treatment plan is to exclusively irradiate the treatment target (tumor) with radiation.

Conventionally, however, two apparatuses are required which include an X-ray computed tomography apparatus for obtaining information such as the position and size of a treatment target and a radiotherapy apparatus. This requires a large installation area and an enormous cost. Furthermore, the position, size, and the like of a treatment target are obtained by the X-ray computed tomography apparatus as a separate apparatus. The patient is then transported to the radiotherapy apparatus which is generally installed in another room, and an irradiation position is set all over again. This leads to a deterioration in positioning precision.

BRIEF SUMMARY OF THE INVENTION

It is an object of the present invention to provide an X-ray computed tomography apparatus which can improve the positioning precision in radiotherapy.

According to the first aspect of the present invention, there is provided an X-ray computed tomography apparatus comprising a first X-ray tube configured to generate X-rays with which a subject to be examined is irradiated, a first X-ray detector configured to detect X-rays transmitted through the subject, a second X-ray tube which generates X-rays with which a treatment target of the subject is irradiated, a rotating mechanism which rotates the first X-ray tube, the first X-ray detector, and the second X-ray tube around the subject, a reconstructing unit configured to reconstruct an image on the basis of data detected by the first X-ray detector, and a support mechanism configured to support the second X-ray tube such that a central axis of X-rays from the second X-ray tube tilts with respect to a body axis of the subject.

According to the second aspect of the present invention, there is provided an X-ray computed tomography apparatus comprising a first X-ray tube configured to generate X-rays with which a subject to be examined is irradiated, a first X-ray detector configured to detect X-rays transmitted through the subject, a second X-ray tube which generates X-rays with which a treatment target of the subject is irradiated, a second X-ray collimator having an aperture which is used to collimate X-rays from the second X-ray tube and whose width and position are variable, a rotating mechanism which rotates the first X-ray tube, the first X-ray detector, and the second X-ray tube around the subject, a reconstructing unit configured to repeat reconstruction of an image based on data detected by the X-ray detector along with rotation of the first X-ray tube and the first X-ray detector, an image processor configured to repeatedly extract a region of the treatment target from the image, and a controller configured to dynamically change the aperture of the collimator upon rotation of the second X-ray tube on the basis of the extracted region of the treatment target.

According to the third aspect of the present invention, there is provided an X-ray computed tomography apparatus comprising a first X-ray tube configured to generate X-rays with which a subject to be examined is irradiated, a first X-ray detector configured to detect X-rays transmitted through the subject, a second X-ray tube configured to generate X-rays with which the subject is irradiated, and a high voltage generator configured to selectively supply power to the first X-ray tube within a first range and selectively supply power to the second X-ray tube within a second range wider than the first range.

According to the fourth aspect of the present invention, there is provided an X-ray computed tomography apparatus comprising a first X-ray tube configured to generate X-rays with which a subject to be examined is irradiated, a first X-ray detector configured to detect X-rays transmitted through the subject, a second X-ray tube configured to generate X-rays with which the subject is irradiated, a first X-ray collimator having an aperture which is used to collimate X-rays from the first X-ray tube and has a width that is variable within a first range, and a second X-ray collimator having an aperture which is used to collimate X-rays from the second X-ray tube and has a width that is variable within a second range wider than the first range.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constituted a part of the specification, illustrate presently preferred embodiments of the invention, and together with the general description given above and the detailed description of the preferred embodiments given below, serve to explain the principles of the invention.

FIG. 1 is a block diagram showing the main part of an X-ray computed tomography apparatus according to an embodiment of the present invention;

DETAILED DESCRIPTION OF THE INVENTION

Figure 2:
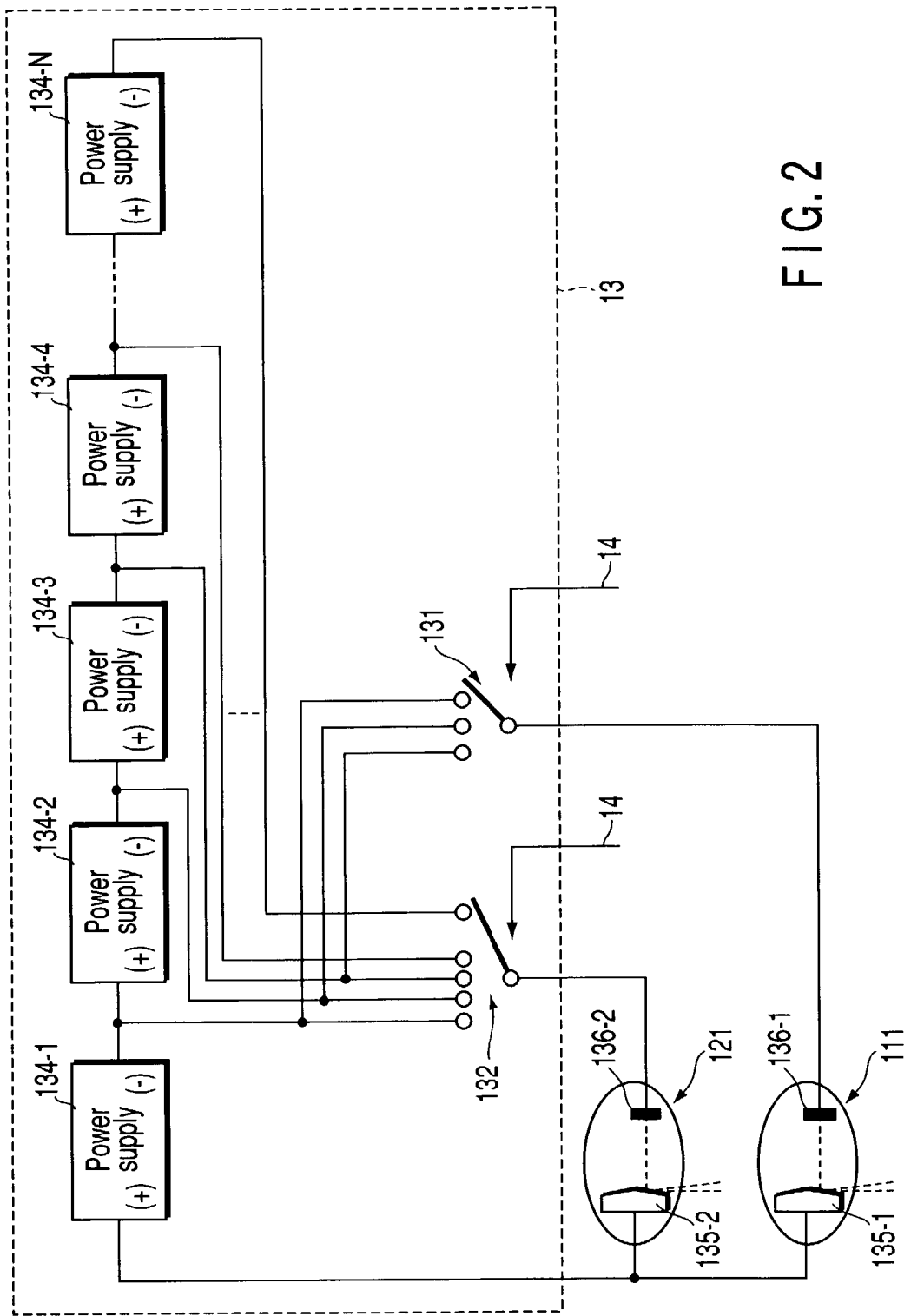
FIG. 2 is a block diagram showing the arrangement of a high voltage generator in FIG. 1.

An X-ray computed tomography apparatus (X-ray CT apparatus) according to a preferred embodiment of the present invention will be described below with reference to the views of the accompanying drawing. Note that the scanning scheme of X-ray computed tomography apparatuses include various types, e.g., a rotate/rotate type in which an X-ray tube and X-ray detector rotate together around a subject to be examined, and a stationary/rotate type in which many detection elements are arrayed in the form of a ring, and only an X-ray tube rotates around a subject to be examined. The present invention can be applied to either type. In this case, the rotate/rotate type will be exemplified. In order to reconstruct one-slice tomographic image data, 360° projection data corresponding to one rotation around a subject to be examined is required, or (180°+ fan angle) projection data is required in the half scan method. The present invention can be applied to either of these reconstruction schemes. The former method will be exemplified here. Note that projection data is defined as integral data associated with the passing distances of attenuation coefficients (or absorption coefficients) of tissue or the line on an X-ray path.

FIG. 1 shows the arrangement of the main part of the X-ray computed tomography apparatus according to this embodiment. The X-ray computed tomography apparatus according to this embodiment is comprised of a scan gantry 1, a computer unit 2, and a bed (not shown). The scan gantry 1 is a constituent element for acquiring projection data associated with a subject to be examined. This projection data is loaded into the computer unit 2 and subjected to processing such as image reconstruction. The subject is inserted into the imaging area of the scan gantry 1 while lying on the table top of the bed.

The computer unit 2 is comprised of a central control unit 21, a preprocessor 23 connected to the central control unit 21 via a data/control bus 22, a reconstructing unit 24, an image displaying unit 25, and an image processor 26.

The scan gantry 1 is of a multi-tube type, i.e., has a plurality of data detection systems, each including an X-ray tube and X-ray detector, mounted on an annular gantry. However, a plurality of data detection systems may be respectively mounted on a plurality of rotating gantries. In this case, the scan gantry 1 will be described as a two-tube type gantry.

The first data detection system 11 has a first X-ray tube assembly 110 and a first multi-channel type X-ray detector 113 which opposes the first X-ray tube assembly 110. A second data detection system 12 has a second X-ray tube assembly 120 and a second multi-channel type X-ray detector 123 which opposes the second X-ray tube assembly 120. A central axis extending from the X-ray focal point of the second X-ray tube assembly 120 of the second data detection system 12 to the center of the second X-ray detector 123 crosses the central axis of the first data detection system 11 at a rotation axis RA at a predetermined angle (assumed to be 90° herein). A first X-ray detector 113 of the first data detection system 11 rotates 90° ahead of the second X-ray tube assembly 120 of the second data detection system 12. The second X-ray tube assembly 120 of the second data detection system 12 follows the first X-ray detector 113 of the first data detection system 11 with a delay of 90°.

The first X-ray tube assembly 110 has a first X-ray tube 111 and a first X-ray collimator 112. The first X-ray collimator 112 is mounted immediately in front of the X-ray radiation window of the first X-ray tube 111. The first X-ray collimator 112 limits the divergence angle (fan angle) of X-rays emitted from the first X-ray tube 111 in the X-ray channel direction. The first X-ray collimator 112 has a plurality of movable shield plates and driving units which separately move the plates. The aperture width and aperture center position can be arbitrarily adjusted by controlling the position of each of the plurality of movable shield plates.

The second X-ray tube assembly 120 has a second X-ray tube 121 and second X-ray collimator 122. The second X-ray collimator 122 limits the divergence angle (fan angle) of X-rays emitted from the second X-ray tube 121. The second X-ray collimator 122 has a plurality of movable shield plates and driving units which separately move the plates. The aperture width and aperture center position can be arbitrarily adjusted by controlling the position of each of the plurality of movable shield plates.

The mechanical restrictions concerning the aperture width on the second X-ray collimator 122 are relaxed as compared with the first X-ray collimator 112. The aperture lower limit (minimum aperture width) of the second X-ray collimator 122 is lower than the that of the first X-ray collimator 112. Note that the aperture upper limit (maximum aperture width) of the second X-ray collimator 122 is almost equal to that of the first X-ray collimator 112. With this arrangement, the second X-ray collimator 122 can increase the fan angle of X-rays to cover the entire area of a slice of the subject and decrease the fan angle to the degree to which the irradiation of X-rays is limited to a relatively small treatment target (tumor) within a slice of the subject.

Figure 3:
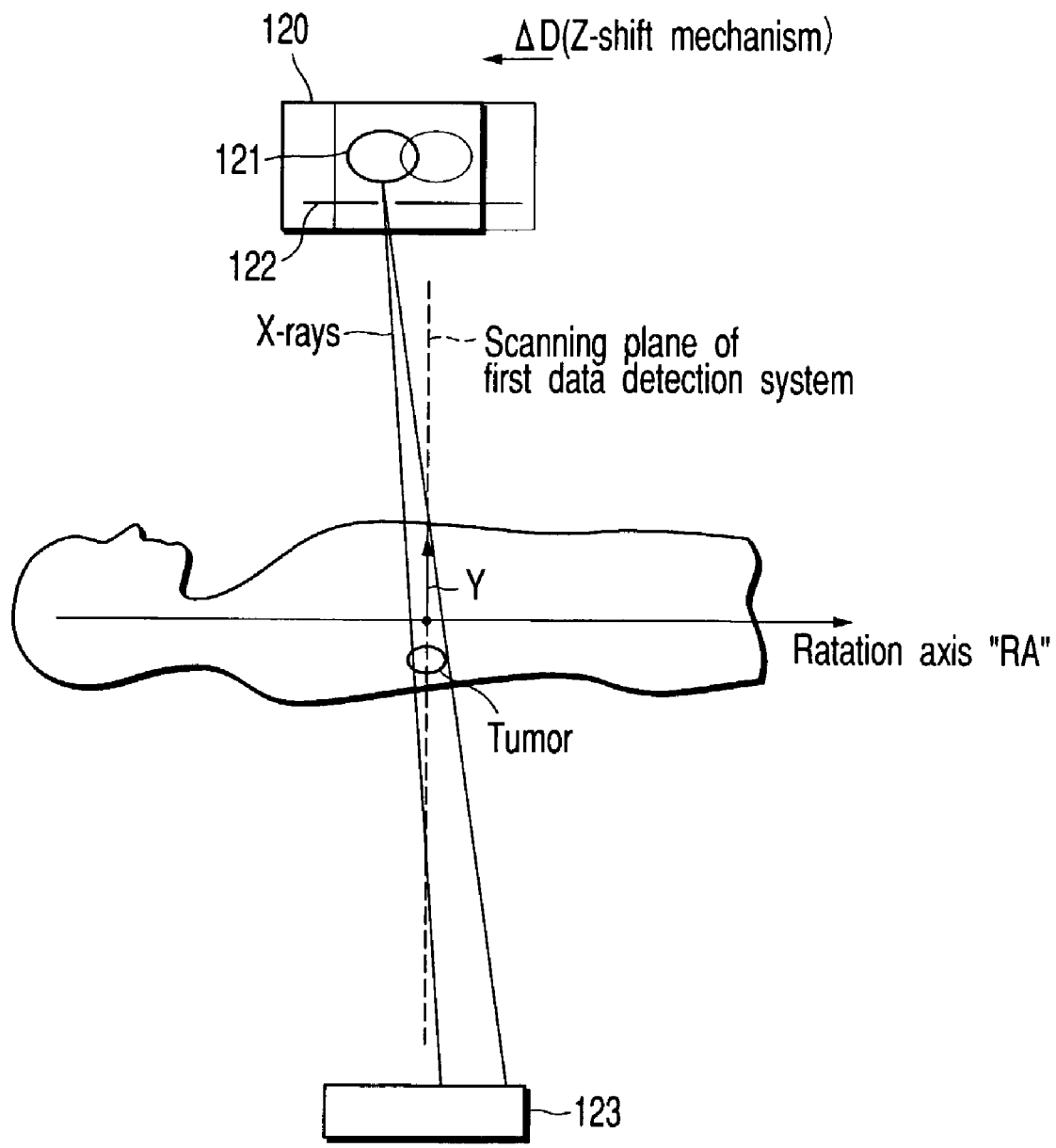
FIG. 3 is a view for explaining the function of a Z-shift mechanism in FIG. 1.

The second X-ray tube assembly 120 is supported by a Z-shift mechanism 15. As shown in FIG. 3, the Z-shift mechanism 15 has a structure and electric driving unit which are necessary to support the second X-ray tube assembly 120 so as to move it in a direction parallel or almost parallel to the rotation axis RA (Z-axis) that almost coincides with the body axis of the subject. The Z-shift mechanism 15 moves the second X-ray tube assembly 120 under the control of a gantry controller 14. Typically, the Z position of the first X-ray tube assembly 110 is so designed as to make the central axis of X-rays emitted from the first X-ray tube assembly 110 in the form of a fan cross the rotation axis RA at a right angle. As a consequence, the X-rays emitted from the first X-ray tube assembly 110 move within a plane (scanning plane) crossing the rotation axis RA at a right angle upon rotation of the gantry. When the Z-shift mechanism 15 does not shift the second X-ray tube assembly 120, the X-ray beam emitted from the second X-ray tube assembly 120 moves within the same scanning plane as that described above upon rotation of the gantry. When the Z-shift mechanism 15 shifts the second X-ray tube assembly 120 by a distance ΔD, the central axis of the X-ray beam emitted from the second X-ray tube assembly 120 obliquely crosses the rotation axis RA, and hence the central axis of X-rays draws a hourglass-like shape having a height ΔD with two cones coupled to each other at their vertexes as the gantry rotates.

FIG. 2 shows an example of the arrangement of a tube voltage generating portion of a high voltage generating unit 13. The high voltage generating unit 13 is shared by the first X-ray tube 111 and second X-ray tube 121. However, high voltage generating units may be respectively provided for the first X-ray tube 111 and second X-ray tube 121. The high voltage generating unit 13 generate a tube voltage to be applied between the anode and the cathode. The high voltage generating unit 13 also generates a filament heating current for heating the filament. The high voltage generating unit 13 includes a plurality of power supplies 134-1, 134-2, . . . , 134-N for boosting the commercial voltage. The power supplies 134-1, 134-2, . . . , 134-N have the same fixed output capacity, e.g., 40 kV. However, the plurality of power supplies 134-1, 134-2, . . . , 134-N need not have the same output performance. For example, the first power supply 134-1 whose positive terminal is connected to anodes 135-1 and 135-2 of the first and second X-ray tubes 111 and 121 may have a capacity of 100 kV, whereas the remaining power supplies 134-2, 134-3, . . . , 134-N may have a capacity of 40 kV.

The negative terminals of the power supplies 134-1, 134-2, and 134-3 are selectively connected to a cathode 136-1 of the first X-ray tube 111 via a selector 131. When the negative terminal of the power supply 134-1 is connected to the cathode 136-1 of the first X-ray tube 111 via the selector 131, a voltage of 40 kV is applied between the anode and cathode of the first X-ray tube 111. When the negative terminal of the power supply 134-2 is connected to the cathode 136-1 of the first X-ray tube 111 via the selector 131, a voltage of 80 kV is applied to the anode and cathode of the first X-ray tube 111. When the negative terminal of the power supply 134-3 is connected to the cathode 136-1 of the first X-ray tube 111 via the selector 131, a voltage of 120 kV is applied to the anode and cathode of the first X-ray tube 111.

The negative terminals of the power supplies 134-1, 134-2, . . . , 134-N are selectively connected to the cathode 136-2 of the second X-ray tube 121 via a selector 132. The voltage applied between the anode and cathode of the second X-ray tube 121 can be changed in steps of 40 kV in the range from 40 kV to (40×N) kV.

The high voltage generating unit 13 has a first filament heating current generator which generates a filament heating current to be supplied of the filament of the first X-ray tube 111, and a second filament heating current generator which generates a filament heating current to be supplied of the filament of the second X-ray tube 121. Each of the first and second filament heating current generators has a high-voltage-insulated transformer. A filament heating current can be changed stepwise in the range from, for example, several mA to several hundred mA by adjusting the primary voltage of the transformer. The output range of the second filament heating current generator is wider than that of the first filament heating current generator. For example, the first filament heating current generator generates filament heating currents in increments of 50 mA within the range from 50 mA to 300 mA. The second filament heating current generator generates filament heating currents in increments of 50 mA within the range from 50 mA to 600 mA.

As described above, the high voltage generating unit 13 has the ability of supplying power to the first X-ray tube 111 within a range suitable for data acquisition and also supplying power to the second X-ray tube 121 within a wide range covering data acquisition and treatment operation.

The high voltage generating unit 13 applies tube voltages and filament heating currents for tube current control to the first and second X-ray tubes 111 and 121 under the control of the gantry controller 14. The gantry controller 14 controls the aperture widths and aperture positions of the first and second X-ray collimators 112 and 122 and all operations associated with scanning, e.g., rotation of the rotating gantry and sliding of the table top, as well as controlling the high voltage generating unit 13.

Outputs from the first and second X-ray detectors 113 and 123 are supplied as projection data to the reconstructing unit 24 via data acquisition systems 114 and 124, a slip ring that allows continuous rotation, and the preprocessor 23. The tomographic data reconstructed by the reconstructing unit 24 is displayed on the image displaying unit 25. The tomographic data acquired by using the first data detection system 11 is sent to the image processor 26 to be used for the extraction of an outline of a treatment target (tumor) region.

As described above, when a higher tube voltage is applied to the second X-ray tube 121 to make a higher tube current flow, and an X-ray beam is further focused by the second X-ray collimator 122, both tomography by the first data detection system and radiotherapy can be realized. This makes it possible to use the same X-ray computed tomography apparatus for tomography, positioning at the time of radiotherapy, and actual radiotherapy. This eliminates the necessity to physically transport the patient and improves the positioning precision.

In addition, since the multi-tube type is used, while radiotherapy is executed by the second data detection system 12, scanning operation for imaging, i.e., irradiation of X-rays and detection of transmitted X-rays under data acquisition X-ray conditions, is performed by the first data detection system 11 to observe tomographic images in real time, and the irradiation position of therapeutic X-rays are sequentially corrected in accordance with the tomographic image as a tumor moves upon movement of the body and the like.

Figure 4:
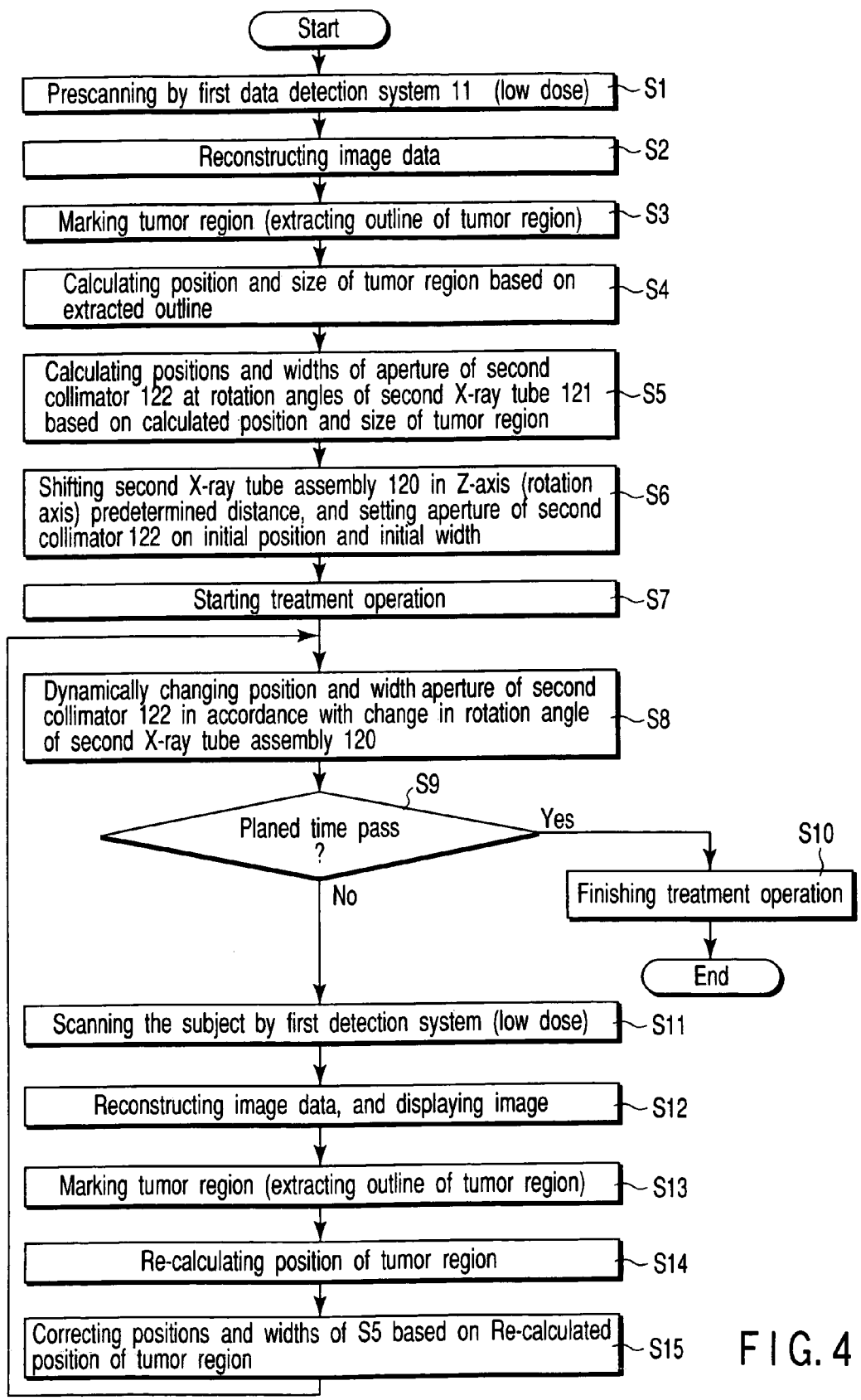
FIG. 4 is a flow chart showing the flow of treatment operation in this embodiment.
Figure 5:
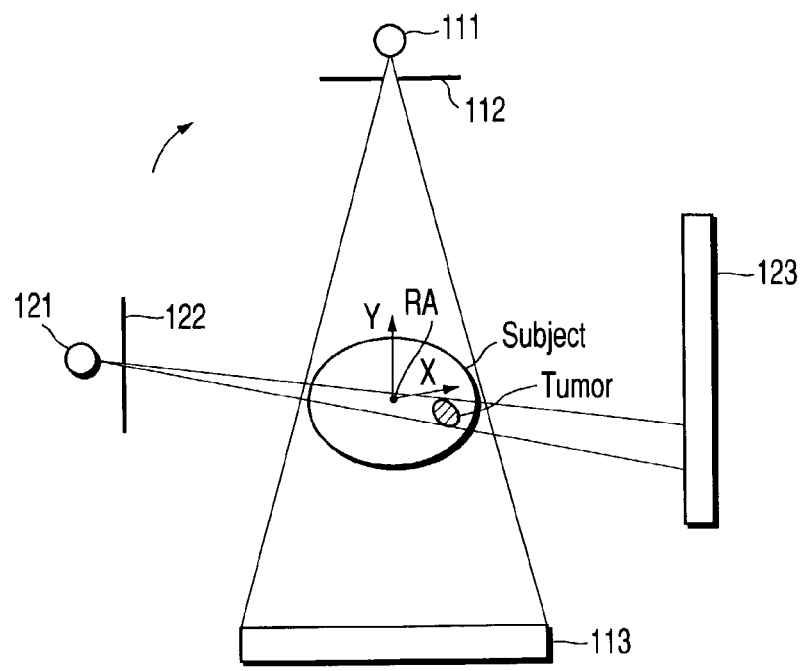
FIG. 5 is a view showing the aperture width and aperture position of the second X-ray collimator when the rotating gantry is at a reference position in this embodiment.
Figure 6:
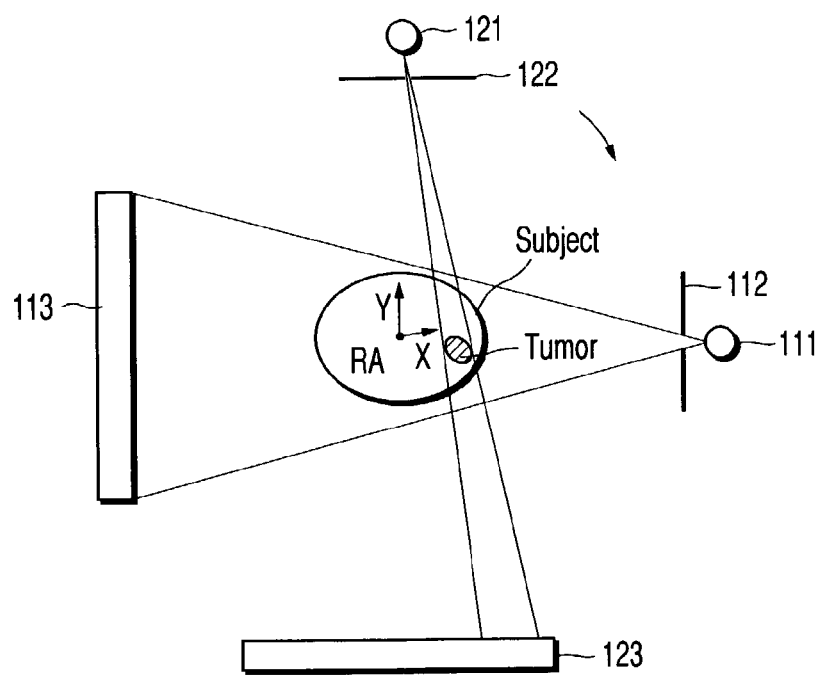
FIG. 6 is a view showing the aperture width and aperture position of the second X-ray collimator when the rotating gantry rotates through 90° from the reference position.
Figure 7:
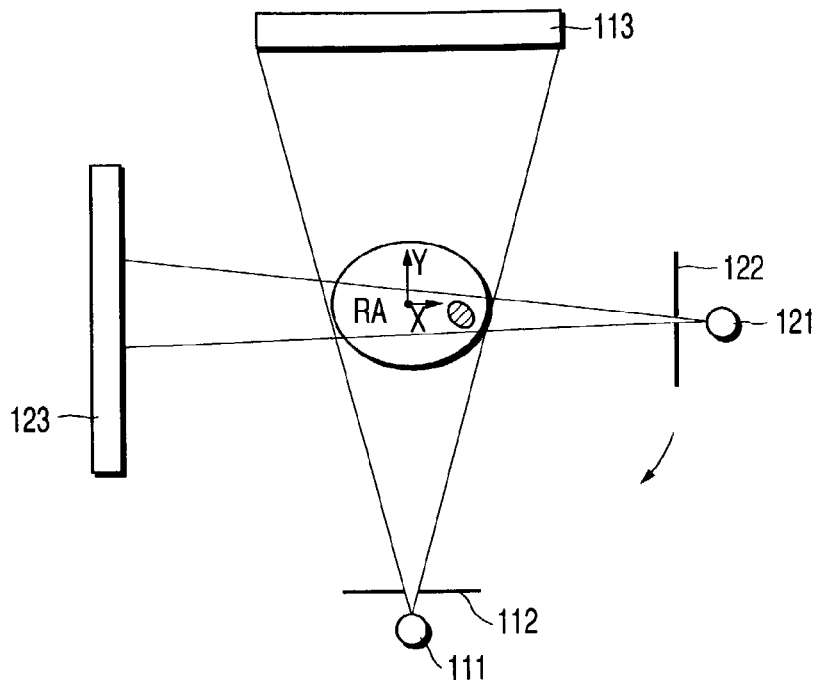
FIG. 7 is a view showing the aperture width and aperture position of the second X-ray collimator when the rotating gantry rotates through 180° from the reference position.
Figure 8:
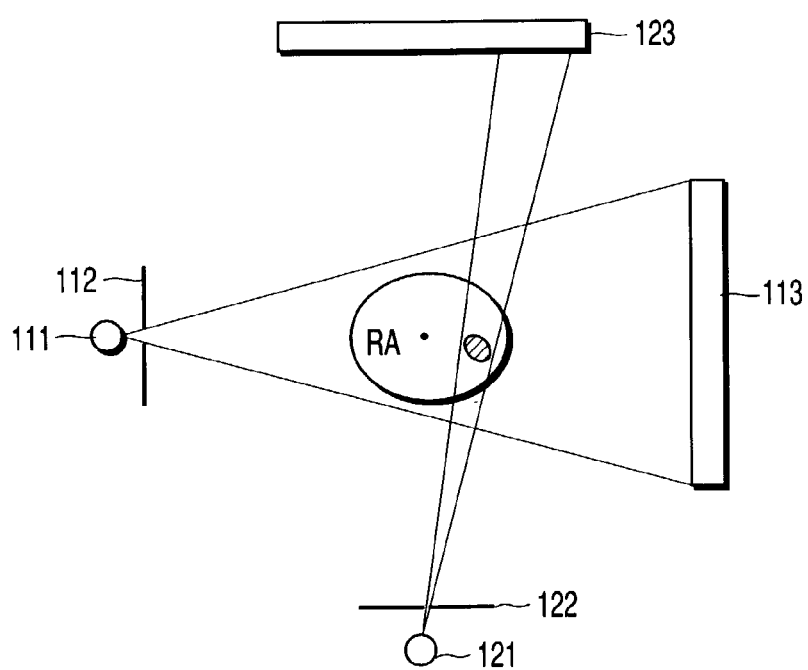
FIG. 8 is a view showing the aperture width and aperture position of the second X-ray collimator when the rotating gantry rotates through 270° from the reference position.

FIG. 4 shows the flow of treatment operation in this embodiment. First of all, preparations are made for treatment operation. The first data detection system 11 executes prescanning for a treatment plan as the first task with a relatively low dose (S1). Obviously, this prescanning operation may be done by using the second data detection system 12 or using both the first and second data detection systems 11 and 12.

Tomographic data is reconstructed by the reconstructing unit 24 on the basis of the projection data in many directions which are acquired by this prescanning (S2). This tomographic image is displayed on the image displaying unit 25. The operator designates a treatment target (tumor) on the displayed tomographic image through an input device (not shown). The image processor 26 extracts an outline of the tumor region by using the point designated by the operator (marking the tumor in step S3). As an outline extracting method, one of the existing methods is arbitrarily selected. Typically, one of the following methods is used: a region enlarging method of recognizing a place exhibiting a specific CT value change as an outline while enlarging a search range outward from the designated point; and an outline tracking method of designating a point on an outline and consecutively tracking points on the outline starting from the designated point as a start point.

The image processor 26 or central control unit 21 calculates the position (center position or baricentric position) of the tumor region and its size on the basis of this extracted outline (S4). The image processor 26 or central control unit 21 further calculates changes in the aperture position and aperture width of the second X-ray collimator 122 with respect to a change in the rotation angle of the second X-ray tube 121 upon rotation of the rotating gantry on the basis of the position and size of the tumor region (S5). More specifically, a predetermined number of discrete points are set at predetermined intervals on the rotation path of the second X-ray tube 121 which corresponds to the Z-shift amount set in treatment operation, and an aperture width and aperture position are calculated at each discrete point such that irradiation of X-rays from the second X-ray tube assembly 120 is limited to a tumor or a tumor and minimum normal tissue around the tumor. Aperture widths and aperture positions corresponding to positions between the discrete points may be adjusted by interpolation or aperture control during treatment operation may be changed in a discrete point passing cycle.

In the final stage of preparatory operation, the aperture width and aperture position of the second X-ray collimator 122 are set to the initial values, i.e., the aperture width and aperture position calculated in step S5 which correspond to a predetermined treatment start rotation angle, under the control of the gantry controller 14 (S6). In step S6, the second X-ray tube assembly 120 is shifted in the Z-axis direction by a predetermined distance. With this Z shift, as described above, therapeutic X-rays from the second X-ray tube assembly 120 move within a hourglass-like shape crossing the scanning plane drawn by data acquisition X-rays from the first X-ray tube assembly 110 only at one point. Therefore, the X-ray dose on a region other than the tumor can be minimized.

After the above preparatory operation is completed, actual treatment operation is started (S7). That is, a corresponding high voltage generator starts to supply power (a tube voltage and filament heating current) to the second X-ray tube 121 under therapeutic X-ray conditions. With this operation, X-rays are emitted from the second X-ray tube 121 at a relatively high dose for treatment operation, and the tumor of the subjected is irradiated with X-rays narrowed into a beam through the narrow aperture of the second X-ray collimator 122. The X-rays may be continuously emitted or intermittently emitted in a pulse-like manner, i.e., in a very short cycle.

As shown in FIGS. 5 to 8, the gantry controller 14 then detects the rotation angle of the second X-ray tube assembly 120 (or second X-ray tube 121) through a position sensor such as a rotary encoder (not shown), and controls second X-ray detector 123 to set an aperture width and aperture position corresponding to the rotation angle in accordance with the calculation result obtained in advance in step S5 (S8).

If a predetermined treatment operation time (irradiation time) has elapsed since the start of the treatment operation (S9), the treatment operation is terminated (S10). That is, in order to stop irradiation of therapeutic X-rays from the second X-ray tube 121 at a relatively high dose, the supply of power (a tube voltage and filament heating current) from the high voltage generator to the second X-ray tube 121 is stopped. If the predetermined treatment operation (irradiation time) has not elapsed since the start of the treatment operation (S9), the flow advances to step S11.

In step S11, the first data detection system 11 scans a scanning plane. More specifically, the high voltage generator starts to supply power (a tube voltage and filament heating current) to the first X-ray tube 111 under data acquisition X-ray conditions. As a consequence, X-rays are emitted from the first X-ray tube 111 at a relatively low dose for data acquisition. The subject is then irradiated with the X-rays at a wide fan angle via the wide aperture of the first X-ray collimator 112, and transmitted X-rays are detected by the first X-ray detector 113. In step S12, tomographic image data is reconstructed by the reconstructing unit 24 in real time on the basis of the detected projection data and displayed (CT fluoroscopy). The image processor 26 extracts the outline of the tumor region on the basis of this tomographic image (S13). The image processor 26 or central control unit 21 re-calculates the position of the tumor region on the basis of this extracted outline (S14).

On the basis of the re-calculated position of the tumor region, a change in the aperture position of the second X-ray collimator 122 with respect to a change in the rotation angle of the second X-ray tube 121 which is calculated in advance is corrected on the basis of the re-calculated tumor region (S15). Although an aperture width may be corrected together with this aperture position, it is preferable that only the aperture position be corrected, in consideration of real-time effect in correction processing.

The flow then returns to step S8 to control the aperture width and aperture position of the second X-ray collimator 122 on the basis of this corrected "change in the aperture position of the second X-ray collimator 122 with respect to a change in the rotation angle of the second X-ray tube 121".

In this manner, tomography is performed and the aperture position of the second X-ray collimator 122 is controlled on the basis of the tumor region extracted from the tomographic image along with treatment operation. This makes it possible to sequentially correct the displacement of the therapeutic X-ray irradiation position with respect to the tumor due to the movement of the body of the patient or the like.

Note that scanning by the first data detection system 11 in step S11 described above may be continuously repeated in a cycle of one rotation, and tomographic image may be repeatedly reconstructed at a frame rate corresponding to one rotation on the basis of the projection data acquired by the reconstructing unit 24 for every rotation. Alternatively, so-called half scanning may be used to increase the frame rate by substantially shortening the scanning interval. In addition, in order to increase the frame rate by substantially shortening the scanning interval, for example, reconstruction processing of adding/subtracting new/old projection data to/from the tomographic image data obtained one cycle ahead at, e.g., every 60° may be used.

Figure 9:
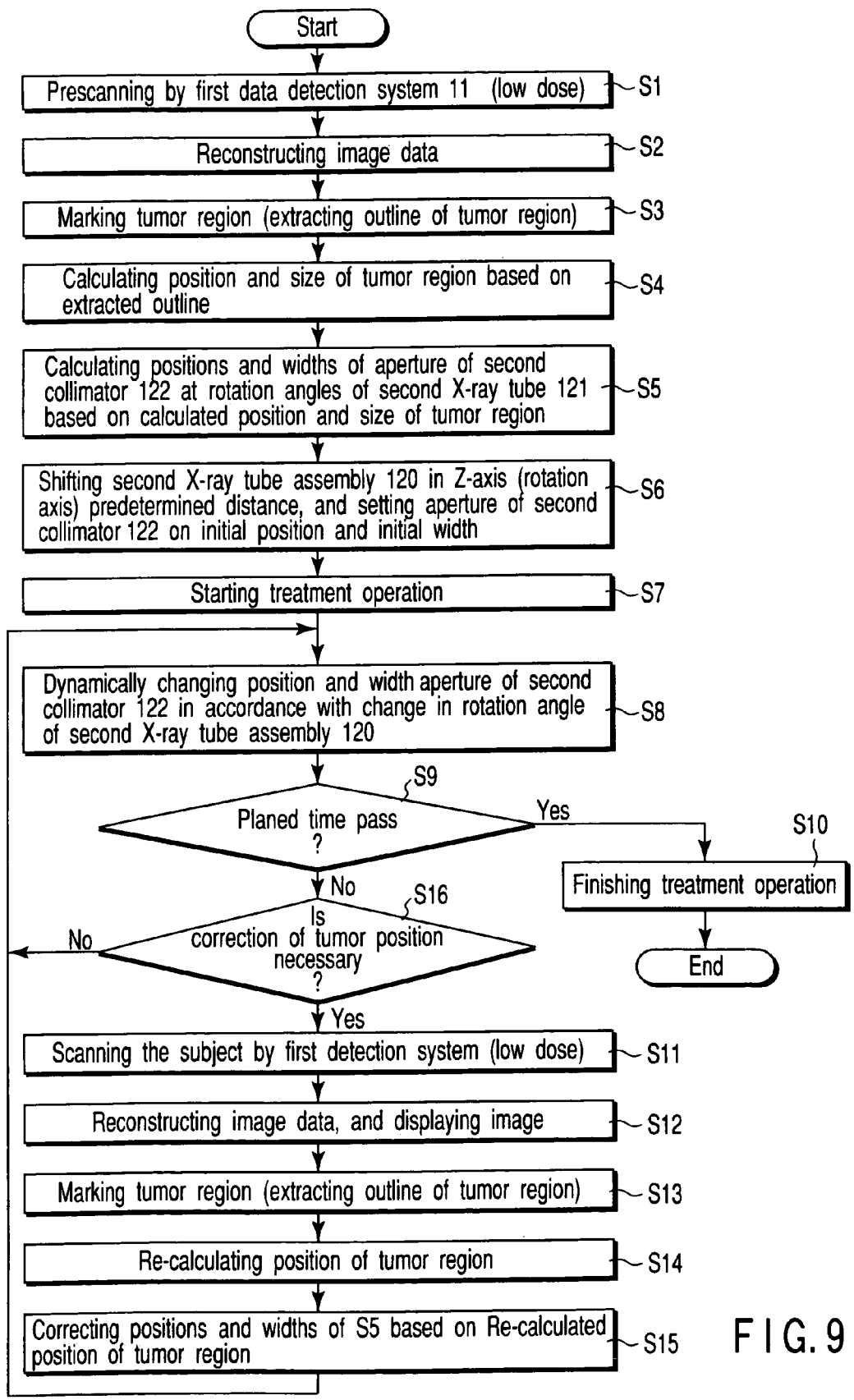
FIG. 9 is a flow chart showing the flow of another treatment operation according to this embodiment.

According to the above description, scanning is continuously performed by the first data detection system 11 in step S11. However, as shown in FIG. 9, in step S16, for example, the movement of the body of the patient may be visually checked, and scanning may be executed only when the position of the tumor needs to be corrected and position correction is manually designated by the operator or may be intermittently executed at predetermined time intervals. This method is effective in reducing the dose for imaging even though the follow-up performance with respect to variations in position slightly deteriorates.

The above description has exemplified the two-tube system. However, the present invention can be applied to a three-tube system or a system with four or more tubes. If, for example, a three-tube system is to be used, data acquisition for tomography may be performed by the first data detection system while treatment operation may be done by using the two tubes of the second and third data detection systems. Alternatively, data acquisition for tomography may be performed by the first and second data detection systems while treatment operation may be done by using the single tube of the third data detection system.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An X-ray computed tomography apparatus, comprising:
    a first X-ray tube configured to generate X-rays with which a subject to be examined is irradiated;
    a first X-ray detector configured to detect X-rays transmitted through the subject;
    a second X-ray tube which generates X-rays with which a treatment target of the subject is irradiated;
    a rotating mechanism which rotates said first X-ray tube, said first X-ray detector, and said second X-ray tube around the subject;
    a reconstructing unit configured to reconstruct an image based on data detected by said first X-ray detector; and
    a support mechanism configured to support said second X-ray tube such that a central axis of X-rays from said second X-ray tube tilts with respect to a body axis of the subject,
    wherein said support mechanism supports said second X-ray tube to allow said second X-ray tube to freely move along the body axis of the subject.

2. An apparatus according to claim 1, further comprising:
    a first X-ray collimator having an aperture which is used to collimate X-rays from said first X-ray tube and has an aperture width that is variable within a first range; and
    a second X-ray collimator which is used to collimate X-rays from said second X-ray tube and has an aperture width that is variable within a second range wider than the first range.

3. An apparatus according to claim 1, further comprising:
    a high voltage generator configured to selectively supply power to said first X-ray tube within a first range and to selectively supply power to said second X-ray tube within a second range wider than the first range.

4. An apparatus according to claim 1, further comprising:
    a second X-ray detector corresponding to said second X-ray tube.

5. An X-ray computed tomography apparatus, comprising:
    a first X-ray tube configured to generate X-rays with which a subject to be examined is irradiated;
    a first X-ray detector configured to detect X-rays transmitted through the subject;
    a second X-ray tube configured to generate X-rays with which a treatment target of the subject is irradiated;
    a second X-ray collimator having an aperture which is used to collimate X-rays from said second X-ray tube and whose aperture width and position are variable;
    a rotating mechanism configured to rotate said first X-ray tube, said first X-ray detector, and said second X-ray tube around the subject;
    a reconstructing unit configured to repeat reconstruction of an image based on data detected by said X-ray detector along with rotation of said first X-ray tube and said first X-ray detector;
    an image processor configured to repeatedly extract a region of the treatment target from the image;
    a controller configured to dynamically change the aperture of said collimator upon rotation of said second X-ray tube based on the extracted region of the treatment target; and
    a first X-ray collimator having an aperture which is used to collimate X-rays from said first X-ray tube and has an aperture width that is variable, the aperture of said first X-ray collimator having a variable range narrower than a variable range of the aperture of said second X-ray collimator.

6. An apparatus according to claim 5, wherein said second X-ray tube is arranged with respect to said first X-ray tube such that said first X-ray tube rotates ahead of said second X-ray tube.

7. An apparatus according to claim 5, wherein said controller is configured to dynamically change at least one of a center position and a width of the aperture of said collimator.

8. An apparatus according to claim 5, wherein the aperture of said first X-ray collimator is set such that X-rays from said first X-ray tube cover an entire slice of the subject, and the aperture of said second X-ray collimator is set to be smaller than the aperture of said first X-ray collimator such that a treatment target of the subject is substantially exclusively irradiated with X-rays from said second X-ray tube.

9. An apparatus according to claim 5, further comprising:
    a second X-ray detector corresponding to said second X-ray tube.

10. An X-ray computed tomography apparatus, comprising:
    a first X-ray tube configured to generate X-rays with which a subject to be examined is irradiated;
    a first X-ray detector configured to detect X-rays transmitted through the subject;
    a second X-ray tube configured to generate X-rays with which the subject is irradiated; and
    a high voltage generator configured to supply power to said first X-ray tube within a first range and to supply power to said second X-ray tube within a second range wider than the first range, wherein
    said high voltage generator includes a plurality of power supplies, a first selector configured to select one of connections between said first X-ray tube and said plurality of power supplies, and a second selector configured to select one of connections between said second X-ray tube and said plurality of power supplies, and
    said apparatus further comprises a controller configured to control said first and second selectors to supply, to said second X-ray tube, power higher than that supplied to said first X-ray tube.

11. An apparatus according to claim 10, further comprising:
    a second X-ray detector corresponding to said second X-ray tube.

12. An X-ray computed tomography apparatus, comprising:
    a first X-ray tube configured to generate X-rays with which a subject to be examined is irradiated;
    a first X-ray detector configured to detect X-rays transmitted through the subject;
    a second X-ray tube configured to generate X-rays with which the subject is irradiated;

a high voltage generator configured to supply power to said first X-ray tube within a first range and to supply power to said second X-ray tube within a second range wider than the first range;

a first X-ray collimator having an aperture which is used to collimate X-rays from said first X-ray tube and has an aperture width that is variable; and a second X-ray collimator having an aperture which is used to collimate X-rays from said second X-ray tube and has an aperture width that is variable, the aperture of said second X-ray collimator having a variable range wider than a variable range of the aperture of said first X-ray collimator.

13. An apparatus according to claim 12, wherein the aperture of said first X-ray collimator is set such that X-rays from said first X-ray tube cover an entire slice of the subject, and the aperture of said second X-ray collimator is set to be smaller than the aperture of said first X-ray collimator such that a treatment target of the subject is substantially exclusively irradiated with X-rays from said second X-ray tube.

14. An X-ray computed tomography apparatus, comprising:

a first X-ray tube configured to generate X-rays with which a subject to be examined is irradiated;

a first X-ray detector configured to detect X-rays transmitted through the subject;

a second X-ray tube configured to generate X-rays with which the subject is irradiated;

a first X-ray collimator having an aperture which is used to collimate X-rays from said first X-ray tube and has an aperture width that is variable within a first range; and a second X-ray collimator having an aperture which is used to collimate X-rays from said second X-ray tube and has an aperture width that is variable within a second range wider than the first range.

15. An apparatus according to claim 14, wherein a minimum width of the aperture of said second X-ray collimator is smaller than a minimum width of the aperture of said first X-ray collimator.

16. An apparatus according to claim 14, wherein a maximum width of the aperture of said second X-ray collimator is substantially equal to a maximum width of the aperture of said first X-ray collimator.

17. An apparatus according to claim 14, further comprising:

a second X-ray detector corresponding to said second X-ray tube.

* * * * *